United States Patent [19]

Tabara

[11] 4,434,232

[45] Feb. 28, 1984

[54] MEASURING VESSELS ANALYSIS UTILIZING FIXED ENZYME

[75] Inventor: Takashi Tabara, Hachioji, Japan

[73] Assignee: Olympus Optical Company Limited, Tokyo, Japan

[21] Appl. No.: 281,216

[22] Filed: Jul. 7, 1981

[30] Foreign Application Priority Data

Jul. 9, 1980 [JP] Japan .................................. 55-93569

[51] Int. Cl.$^3$ .......................... C12M 1/40; C12M 1/34
[52] U.S. Cl. .................................... 435/288; 435/291; 435/296
[58] Field of Search ................. 435/40, 288, 291, 296, 435/310

[56] References Cited

U.S. PATENT DOCUMENTS

| | | | |
|---|---|---|---|
| 3,701,716 | 10/1972 | Deuringer et al. | 435/291 X |
| 3,838,011 | 9/1974 | Hagen et al. | 435/291 X |
| 4,147,752 | 4/1979 | Suovaniemi et al. | 435/288 X |
| 4,210,418 | 7/1980 | Brown et al. | 435/296 |
| 4,224,405 | 9/1980 | Hijikata | 435/288 X |
| 4,272,478 | 6/1981 | Vihko | 435/296 X |
| 4,276,048 | 6/1981 | Leaback | 435/296 X |
| 4,314,030 | 2/1982 | Habich | 435/296 |

*Primary Examiner*—Robert A. Yoncoskie
*Attorney, Agent, or Firm*—Parkhurst & Oliff

[57] ABSTRACT

A measuring vessel for analysis utilizing a fixed enzyme is disclosed. This vessel has an inner peripheral surface at least a part of which being provided with at least one fixed enzyme, and a movable bottom portion. By applying this measuring vessel to automatic biochemical analyzing apparatus can be performed not only single channel-single item analysis but also single channel-multi item analysis.

15 Claims, 5 Drawing Figures

MEASURING VESSELS ANALYSIS UTILIZING FIXED ENZYME

This invention relates to a measuring vessel for analysis utilizing a fixed enzyme, and more particularly to an application of this measuring vessel to an automatic biochemical analyzing apparatus.

Heretofore, enzymes have been used for qualitative and quantitative analyses of a certain substance owing to its substrate specificity and they are widely utilized in biochemical fields because they have a high analytical sensitivity. Since the enzyme is expensive, there have been various improvements for repeatedly and stably using the enzyme over a long period. As a result, the utilization of fixed enzymes formed by fixing enzyme onto an insoluble solid has lately become popular. In automatic analyses are used a flow system in which enzyme is fixed to an inner surface of a nylon tube, the flow system having a column filled with enzyme-fixed beads, an electrode system having a fixed enzyme film and the like. These systems are suitable for single channel-single item analysis, but are unsuitable for single channel-multi item analysis. When using the flow system for multi item analysis, carry-over is still existent as a latent problem. The case of the electrode system, it is necessary to use one fixed enzyme film and one indicating or measuring electrode for every one item, so that plural fixed enzyme films and electrodes are required for multi item analysis. As a result, the electrode system for multi item analysis is not useful for economic reasons and inefficiency.

It is, therefore, an object of the invention to solve the aforementioned drawbacks of the conventional measuring vessel utilizing a fixed enzyme and to provide a measuring vessel for analysis utilizing a fixed enzyme which is applicable to an automatic biochemical analyzing apparatus for not only single item but also multi item analyses.

According to the invention, there is provided a measuring vessel for analysis utilizing a fixed enzyme, characterized in that said vessel has an inner peripheral surface at least a part of which being provided with at least one fixed enzyme, and a movable bottom portion.

The invention will now be described in detail with reference to the accompanying drawings, wherein.

Figure 1:
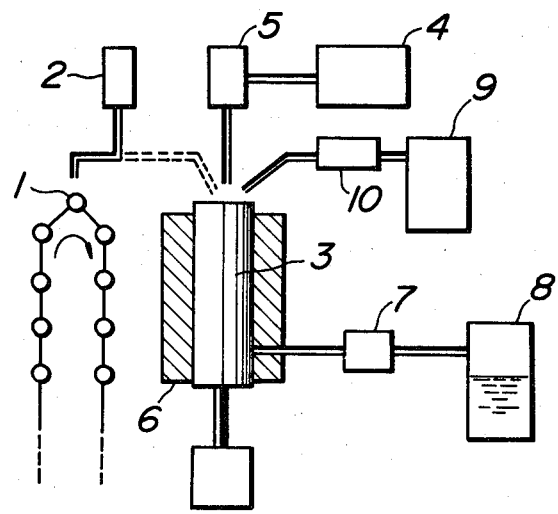
FIG. 1 is a schematic view illustrating the whole of biochemical analyzing apparatus provided with an embodiment of the measuring device according to the invention.

In FIG. 1 is schematically shown an automatic biochemical analyzing apparatus provided with an embodiment of the measuring vessel according to the invention as a whole.

In this figure, numeral 1 is a sample cup intermittently transported on a sample line in the arrow direction. Numeral 2 is a sample pipetting member, which delivers a given amount of sample liquid contained in the same cup 1 into a reaction tube 3. This reaction tube 3 is a measuring vessel according to the invention. On the other hand, a reagent contained in a reagent tank 4 is delivered into the reaction tube 3 by means of a reagent pipetting member 5. The reaction tube 3 is thermostated in a thermostatic chamber 6. In the reaction tube 3, the sample liquid and reagent react with each other. Such a reaction liquid is measured by, for example, an ion-sensitive electrode method, a spectroscopic analysis or the like, a measured value of which is supplied as an electric signal into a measuring circuit (see FIG. 2A), where the signal is converted into a value of concentration and outputted therefrom. After completion of the measurement, the reaction liquid existent in the reaction tube 3 is discharged into a waste tank 8 through a drain pump 7. Then, washing water is charged from a water tank 9 through a pump 10 to the reaction tube 3 to clean the inside of the reaction tube 3. Thereafter, the washed water is discharged into the waste tank 8 through the drain pump 7.

Figure 2A:
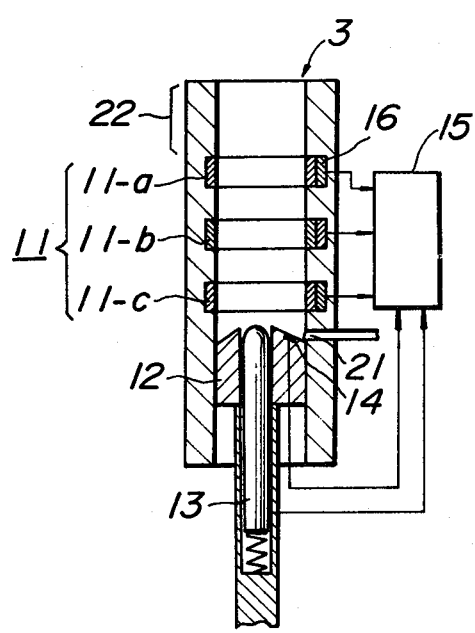
FIGS. 2A and 2B are schematic sectional views of the measuring vessel according to the invention, respectively.
Figure 2B:
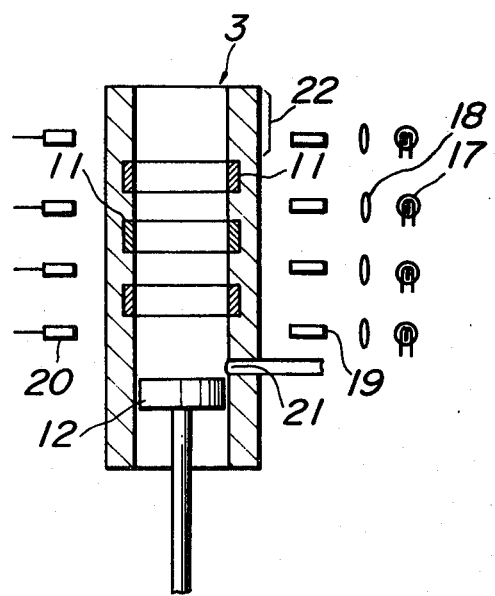

In FIGS. 2A and 2B are schematically shown sectional views of embodiments of the measuring vessel according to the invention, respectively.

The measuring vessel or reaction tube 3 according to the invention may take various shapes, but in the illustrated embodiment it is a hollow cylindrical shape. On at least a part of the inner peripheral surface of the reaction tube 3 is formed a band 11 of a fixed enzyme. In the illustrated embodiment, three fixed enzyme bands 11-a, 11-b and 11-c are disposed at axially proper intervals on the inner peripheral surface of the reaction tube 3, wherein the enzymes to be fixed are different in kind. Further, the reaction tube 3 has a bottom portion 12 which is movable in the up-and-down direction. Therefore, this bottom portion 12 can be moved to a proper position inside the reaction tube 3 in compliance with the measuring item, liquid discharging and washing.

FIG. 2A shows an embodiment of the reaction tube 3 to be used in the ion-sensitive electrode method. In this case, the bottom portion 12 of the reaction tube 3 is provided with a measuring or indicating electrode 13 and a reference electrode 14 each being connected to a measuring circuit 15. Furthermore, each fixed enzyme band 11 is disposed on a corresponding ion sensitive film formed on a gate portion of an ion-selective field effect transistor (ISFET) 16, which is embedded at an axially predetermined position in the reaction tube wall and connected to the measuring circuit 15. In order to effectively develop the function of the ISFET 16, the fixed enzyme band 11 must be porous or have plural apertures formed therein. Alternatively, the ISFET or an ion sensitive electrode may be arranged above and below each fixed enzyme band apart therefrom.

FIG. 2B shows an embodiment of the reaction tube 3 to be used in the spectroscopic analysis. In this case, the reaction tube wall is transparent and three fixed enzyme bands 11 are disposed on the inner peripheral surface of the tube at axially predetermined intervals. Further, light sources 17, lenses 18, interference filters 19 each having a different transmittance, and light-receiving elements 20 are arranged on both sides of the reaction tube 3.

In the operation of the reaction tube 3, when the analytical item utilizes the fixed enzyme, the bottom portion 12 is first moved to such a position that the sample liquid and reagent to be charged into the reaction tube 3 are sufficiently contacted with a necessary fixed enzyme band 11. Then, the sample liquid and reagent are charged through the pipetting members into the reaction tube 3, where they are contacted with the enzyme to conduct a reaction required for a given item. After the completion of the reaction, the measurement is carried out with respect to the reaction liquid. After the completion of the measurement, the bottom portion 12 is moved to such a position that the reaction liquid may be discharged from a discharge port 21 through the drain pump 7 into the waste tank 8 to thereby perform the liquid discharging and washing.

In the case of an analytical item not utilizing the fixed enzyme, that portion of the reaction tube 3 having no fixed enzyme at its inner peripheral surface or an enzyme-absent portion 22 is used. In this case, the bottom portion 12 of the reaction tube 3 is first moved to a position wherein the sample liquid and reagent to be charged into the tube are never contacted with the fixed enzyme band 11. Then, the sample liquid and reagent are charged through the pipetting members into the reaction tube 3, where they react with each other without contacting the fixed enzyme. The procedure after the completion of the reaction is the same as described for the analytical item utilizing the fixed enzyme.

Accordingly, single channel-multi item analysis can be performed by repeating the above mentioned procedure every item in the measuring vessel or reaction tube according to the invention. Moreover, when the reaction tube wall corresponding to the enzyme-absent portion 22 is transparent, colorimetric analysis can also be performed.

Next, the invention will be described with respect to the measurement using similar reagents, which do not interfere with each other.

In general, it is known that all of glucose, cholesterol, neutral fat, phospholipid, uric acid and the like react with an oxidizing enzyme to produce hydrogen peroxide. Therefore, when measuring these substances by using the similar reagents, the procedure of sample charging→reagent charging→measurement of item a→measurement of item b→liquid discharging→washing is performed instead of repeating the procedure with every item of sample charging→reagent charging-→measurement→liquid discharging→washing as mentioned above, whereby multi items can be measured continuously.

For instance, when the free cholesterol content and the total cholesterol quantity of the sample liquid are continuously measured by using the measuring vessel according to the invention (FIG. 2A), the bottom portion 12 of the reaction tube is first moved to a position corresponding to a fixed enzyme band 11-a containing cholesterol oxidase. Then, the sample liquid and given reagent (phosphoric buffer solution) are charged into the reaction tube 3, where free cholesterol in the sample liquid is oxidized to produce hydrogen peroxide. The amount of hydrogen peroxide produced is measured by using the measuring electrode 13 embedded in the bottom portion 12 (Measurement of free cholesterol quantity).

Thereafter, the bottom portion 12 is moved downward to a position corresponding to a fixed enzyme band 11-b containing cholesterol ester hydrase and cholesterol oxidase, whereby ester-type cholesterol in the sample liquid is hydrolyzed and oxidized to produce hydrogen peroxide. The amount of hydrogen peroxide produced is again measured by the measuring electrode 13. This measured value is combined with the measured value for free cholesterol to determine a total cholesterol value (Measurement of total cholesterol quantity).

In the above continuous measurement, when the amount of the reagent required for the second item is deficient or if it is intended to require a larger amount of the reagent for the second item as against the reagent for the first item, supplemental amount of the reagent for the second item may be added after the downward movement of the bottom portion 12 prior to the measurement of the second item, so that the measurement can rapidly correspond to the change of reagent amount of each item.

Figure 3A:
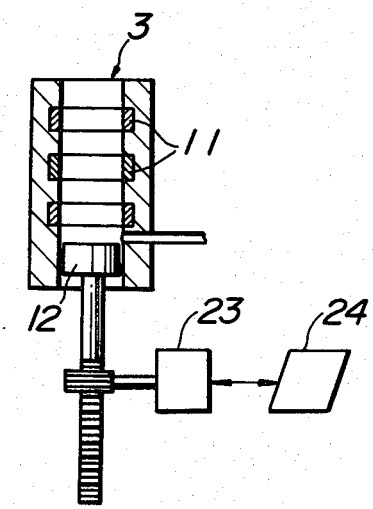
FIGS. 3A and 3B are schematic sectional views of the measuring vessel provided at its bottom with a driving mechanism according to the invention, respectively.
Figure 3B:
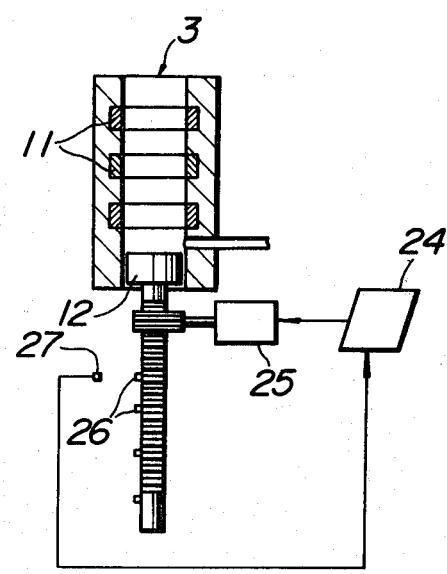

In FIGS. 3A and 3B are schematically shown sectional views of embodiments of the measurement vessel or reaction tube according to the invention provided at the bottom with a driving mechanism for the bottom portion.

FIG. 3A shows an embodiment of the reaction tube 3 wherein a stepping motor 23 connecting to a motor controlling circuit 24 is mounted to the bottom portion 12 as a driving mechanism.

FIG. 3B shows an embodiment of the reaction tube 3 wherein a reversible motor 25 is mounted to the bottom portion 12 as a driving mechanism. Since the reversible motor 25 moves the bottom portion 12 of the reaction tube 3 upward and downward, the driving of this motor is controlled by detecting with a photo sensor 27; radiation from a photo diode 26, which is installed on an elevating drive shaft protruding downwardly from the bottom portion 12 at a position corresponding to each stop position of the bottom portion, whereby the movement of the bottom portion 12 is controlled.

In the measuring vessel according to the invention, the bottom portion can be moved upward and downward by means of any well-known driving mechanism in addition to the use of the above mentioned motor.

In the measuring vessel for analysis utilizing the fixed enzyme according to the invention, at least one fixed enzyme is adhered to at least a part of the inner peripheral surface of the vessel, so that economical utilization of the reagent can be attained while maintaining various advantages based on the use of the conventional fixed enzyme and the stability and preservation of the reagent are facilitated. Further, the invention makes it possible to perform not only single channel-single item analysis but also single channel-mutli item analysis. Moreover, the measuring vessel according to the invention is provided at its bottom with a driving mechanism for the bottom portion, so that the position of the bottom portion can be moved in accordance with the analytical item, such as an item not utilizing an enzyme, an item utilizing a certain enzyme and the like, and in some cases rapid and continuous measurement can be performed. In the washing of the measuring vessel, the bottom portion can easily be moved downward by the driving mechanism to the discharge port for washing water, so that the preceding sample and reagent, which are a cause of contamination, may be removed from in the vessel, whereby precise measurement can be performed. When the measuring vessel according to the invention having the above merits is applied to automatic biochemical analyzing apparatus, not only single channel-multi item analysis can be attained, but also economically obtained accurate analytical value and the like can be improved.

What is claimed is:

1. A measuring vessel for analysis utilizing a fixed enzyme, said vessel comprising an inner wall surface at least a part of which is provided with at least one fixed enzyme, and an impervious bottom member movable substantially vertically within the vessel for locating liquid in the vessel at a predetermined level within the vessel.

2. A measuring vessel as claimed in claim 1, wherein two or more fixed enzymes are disposed on said inner wall surface of said vessel spaced from each other in the top-to-bottom direction of the vessel.

3. A measuring vessel as claimed in claim 1, wherein the wall of said vessel is transparent.

4. A measuring vessel as claimed in claim 1, wherein said bottom member is provided with an ion concentration measuring electrode and a reference electrode.

5. A measuring vessel as claimed in claim 1, wherein an ion-selective field effect transistor is embedded in the wall of said vessel at a position corresponding to the position of said fixed enzyme.

6. A measuring vessel for automatic analysis using a fixed enzyme, comprising:
a container member for holding fluids, at least a portion of the inner surface of said container member having a fixed enzyme located thereon, said container member being open at its top and bottom;
and an impervious bottom member for holding fluids in said container member, said bottom member being movable up and down within said container member for locating liquid in the container member at a predetermined level within the container member.

7. The measuring vessel of claim 6 wherein there are a plurality of fixed enzymes located on said inner surface at different positions in the top-to-bottom direction of the container.

8. The measuring vessel of claim 7 wherein each of said plurality of fixed enzymes is located in a band around the inner circumference of the container.

9. The measuring vessel of claim 6, wherein the fixed enzyme is in the form of a porous layer disposed over an ion sensitive film formed on a gate portion of an ion-selective field effect transistor, and the bottom member includes a measuring electrode and a reference electrode exposed for contacting fluid in said vessel.

10. The measuring vessel of claim 6, wherein the fixed enzyme is in the form of a layer disposed immediately adjacent an ion sensitive film formed on a gate portion of an ion-selective field effect transistor, and the bottom member includes a measuring electrode and a reference electrode exposed for contacting fluid in said vessel.

11. The measuring vessel of claim 9 or 10, wherein there are a plurality of fixed enzymes located on the inner surface at different positions in the top-to-bottom direction of the container.

12. The measuring vessel of claim 9 or 10, wherein there are a plurality of fixed enzymes located in bands around the inner circumference of the container and located at different positions in the top-to-bottom direction of the container.

13. The measuring vessel of claim 6, 7, or 8 wherein the container member is transparent.

14. The measuring vessel of claim 7 or 8, wherein the bottom member is connected to driving means for moving said bottom member in the top and bottom directions, within the container member.

15. The measuring vessel of claim 14 wherein said driving means is controlled by photo radiation-detection means for stopping said bottom member at a location where fluid in said vessel will be in contact with one of said fixed enzymes.

* * * * *